(12) United States Patent
Ueno

(10) Patent No.: US 6,561,025 B2
(45) Date of Patent: May 13, 2003

(54) SPECIFIC GRAVITY MEASURING DEVICE

(75) Inventor: Sakujiro Ueno, Osaka (JP)

(73) Assignee: Mirage Trading Co., Ltd., Osaka (JP)

( * ) Notice: Subject to any disclaimer, the term of this patent is extended or adjusted under 35 U.S.C. 154(b) by 0 days.

(21) Appl. No.: 10/075,902

(22) Filed: Feb. 13, 2002

(65) Prior Publication Data

US 2002/0117002 A1 Aug. 29, 2002

(30) Foreign Application Priority Data

Feb. 14, 2001 (JP) ........................................ 2001-037282

(51) Int. Cl.[7] ................................................ G01N 9/08
(52) U.S. Cl. ........................................ 73/437; 73/32 R
(58) Field of Search ............................... 73/433, 32 R, 73/451, 452, 453, 437

(56) References Cited

U.S. PATENT DOCUMENTS

| | | | |
|---|---|---|---|
| 3,747,416 A | * 7/1973 | Wommack | 73/437 |
| 4,175,426 A | * 11/1979 | Rosenblum | 73/438 |
| 4,372,405 A | * 2/1983 | Stuart | 177/207 |
| 4,770,041 A | * 9/1988 | Bearce | 177/207 |
| 5,076,107 A | * 12/1991 | Timmermans et al. | 177/50 |

* cited by examiner

Primary Examiner—Hezron Williams
Assistant Examiner—Tamiko Bellamy
(74) Attorney, Agent, or Firm—Goodwin Procter LLP

(57) ABSTRACT

A specific gravity measuring device can certainly and instantly measure specific gravity of various solid state substances through one measurement operation quite simply. The specific gravity measuring device includes a liquid bath, a first measuring portion supporting the liquid bath, a measuring object receptacle member arranged in the liquid bath in a condition dipped in the liquid, a second measuring portion supporting the measuring object receptacle member in non-contact condition relative to the liquid bath, an arithmetic unit deriving a specific gravity value on the basis of measured values of the first and second measuring portions and a display unit for displaying the specific gravity value derived by the arithmetic unit. The first measuring portion measuring increase of weight associating with dipping of the measuring object in the liquid by the first measuring portion, as buoyancy, and the second measuring portion measures a weight of the measuring object in the liquid by the second measuring portion. The arithmetic unit derives the specific gravity value from a measured value of the buoyancy and the weight in liquid for displaying on the display unit.

13 Claims, 3 Drawing Sheets

SPECIFIC GRAVITY MEASURING DEVICE

BACKGROUND OF THE INVENTION

1. Field of the Invention

The present invention relates to a specific gravity measuring device to be used for measurement of various substance including not only solid substance consisted of wide variety of solid materials including noble metal, alloy, synthetic resin, ceramics, rubber, fiber and so forth, but also powder state substances, granular state substances, liquid state substances.

2. Description of the Related Art

In general, in order to know specific gravity of solid state substance having unknown volume, the volume of the solid state substance is, at first, derived utilizing Archimedes principle. Namely, using a principle that buoyancy of substance in a fluid is equal to a weight of the fluid detruded by the solid state substance, a weight of the solid state substance in air and a weight in liquid are measured in the condition completely sinking in the liquid having known specific gravity (normally, water having specific gravity 1) to derive a volume of the solid state substance from the buoyancy (g) as difference of the weight in air and the weight in liquid, and a specific gravity (g/cm$^3$) of the liquid. Then, the specific gravity of the objective solid state substance is derived as weight in air (g)/volume (cm$^3$). When the liquid to be used is water, since the weight (g) thereof is equal to a value of the volume (cm$^3$), the value of buoyancy (g) matches with the value of volume (cm$^3$) of measuring object as is. Accordingly, specific gravity (g/cm$^3$) of the measuring object can be expressed by the following equation.

Specific Gravity=Weight in Air/Buoyancy=Weight in Air/(Weight in Air)−(Weight in Water)

The conventional specific gravity measuring device includes a first container containing a liquid, a second container disposed in the first container in non-contact manner and permitting the liquid in the first container flowing in and out, an aerial mounting portion supported in the second container for measuring weight of the measuring object in air, and a weighting equipment receiving and supporting the second container to derive and display specific gravity from the weight when the measuring object as mounted on the aerial mounting portion and the weight when the measuring object is sunk within the second container. On the other hand, as the conventional specific gravity measuring device, it has been known a device including a main body of the weighting machine having a hook, and a lifting platform lifting a container filled with water up and down. At first, the measuring object is hanged by the hook to measure the weight in air, then the lifting platform is lifted up to completely sink the measuring object in water for measuring the weight in water for deriving the specific weight from both measured weight to display.

Furthermore, there is another specific gravity measuring device which has a construction to measure buoyancy instead of measuring the weight in water (liquid). Such device is constructed by placing the aerial mounting portion within the first container filled with the liquid and disposing the second container permitting liquid flowing in and out, within the first container in non-contact manner to measure the weight when the measuring object is mounted on the aerial mounting portion by receiving and supporting the weighting equipment the first container. With such device, after measuring the weight of the measuring object as mounted on the aerial mounting portion, the weight of the first container is measured in the condition where the measuring object is sunk in the water in the second container for deriving buoyancy to derive the specific gravity from the buoyancy and the weight in air.

Measurement of specific gravity is exclusively used as means for knowing purity of substance. In the recent years, associating with highly advancing of industrial technology, measurement of specific gravity is frequently used for quality assurance, analysis and so forth of substance, such as noble metal, alloy, synthetic resin, ceramics, rubber, fiber, solid state substance formed of composite material of these, and further even substance including powder state substance, granular state substance. However, since the measurement of specific gravity is means for basic test, inspection and measurement, it is an item to eliminate work load in viewpoint of production ability of the substance while it is important. All of the conventional specific gravity measuring device requires two stage measurement by measurement of weight of the measuring object in air and measurement of weight or buoyancy of measuring object in water (liquid) by sinking the measuring object in water (liquid) to require labor hour and substantial measuring period. Particularly, when measurement of specific gravity is performed for different measuring objects sequentially, the conventional devices are quite inefficient.

SUMMARY OF THE INVENTION

Accordingly, it is the first object of the present invention to provide a specific gravity measuring device which can certainly and instantly measure specific gravity of various solid state substances through one measurement operation quite simply.

A second object of the present invention is to provide a specific gravity measuring device which does not require measurement of weight of measuring object in air, can simultaneously measure a weight in liquid and a buoyancy by two measuring portion only by mounting the measuring object on a measuring object receptacle member in sinking condition within a liquid bath for deriving and displaying specific gravity from result of measurement so that specific gravities of various substances can be quite simply, instantly and certainly measured by one measurement operation, and can be particularly efficient when specific gravities of various measuring objects are measured sequentially.

Other objects and advantages will become clear from the following discussion in terms of the preferred embodiment.

In order to accomplish the above-mentioned and other objects, a specific gravity measuring device, according to the first aspect of the present invention, comprises:

a liquid bath filled with a liquid;

a first measuring portion receiving and supporting the liquid bath;

a measuring object receptacle member arranged in the liquid bath in a condition dipped in the liquid;

a second measuring portion supporting the measuring object receptacle member in non-contact condition relative to the liquid bath:

an arithmetic unit deriving a specific gravity value on the basis of measured values of the first and second measuring portions; and a display unit for displaying the specific gravity value derived by the arithmetic unit;

the measuring object being mounted on the measuring object receptacle member sinking in the liquid within the liquid bath in a condition sinking in the liquid, the first measuring portion measuring increase of weight associating with dipping of the measuring object in the liquid by the first measuring portion, as buoyancy;

the second measuring portion acting simultaneously with the first measuring portion and measuring a weight of the measuring object in the liquid by the second measuring portion;

the arithmetic unit deriving the specific gravity value from a measured value of the buoyancy and the weight in liquid for displaying on the display unit.

In the preferred construction, the arithmetic means is provided with arithmetic correction means. The measuring object receptacle member may be porous member, such as net form member.

Also, the first measuring portion, the second measuring portion, the arithmetic unit and the display unit may be integrally assembled in a main body of weighting equipment, and the measuring object receptacle member nay be hanged by hanging member vertically extending from the second measuring portion. The main body of the weighting equipment may be constructed with a first weighting equipment forming the first measuring portion and a second weighting equipment forming the second measuring portion, the first and second weighting equipments may be integrally connected by a connection frame with defining a gap portion there between. Also, the hanging member may be a wire member including a lower horizontal member fixed to a receptacle seat of the second measuring portion, a support member extending upwardly from the lower horizontal member and an upper horizontal member extending from upper end portions of the support member beyond an upper edge of the liquid bath and extending horizontally in opposition to an upper surface of the liquid bath. The measuring object receptacle member may be hanged by a cable connected to the upper horizontal member at the upper portion and depending into the liquid bath.

The specific gravity measuring device may further comprise a floating preventing member for holding a measuring object lighter than the liquid in the liquid bath on the measuring object receptacle member in sinking condition.

According to the second aspect of the present invention, a specific gravity measuring device comprises:

a liquid bath filled with a liquid having known specific gravity;

measuring object mounting means disposed within the liquid bath for mounting a measuring object in a condition sinking in the liquid;

first measuring means for directly receiving weight of the liquid bath and deriving a buoyancy indicative value representative of buoyancy of the measuring object on the basis of a weight increase when the measuring object is placed on the measuring object mounting means and known specific gravity of the liquid;

second measuring means for supporting the measuring object mounting means, directly receiving weight of the measuring object mounting means and the measuring object as placed on the former and deriving a weight in liquid indicative value representative of weight of the measuring object in water;

arithmetic means for receiving the buoyancy indicative value and the weight in liquid indicative value for deriving a specific gravity indicative value representative of specific gravity of the measuring object; and display means for displaying the specific gravity indicative value.

In the preferred construction, the specific gravity measuring device may further comprises initial setting means for setting initial value of the buoyancy indicative value and the weight in liquid indicative value in a condition where the measuring object is not loaded on the measuring object mounting means.

The second measuring means may support the measuring object mounting means in floating condition relative to the liquid bath.

The specific gravity measuring device may further comprise retainer means for retaining the measuring object on the measuring object mounting means.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of a specific gravity measuring device according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
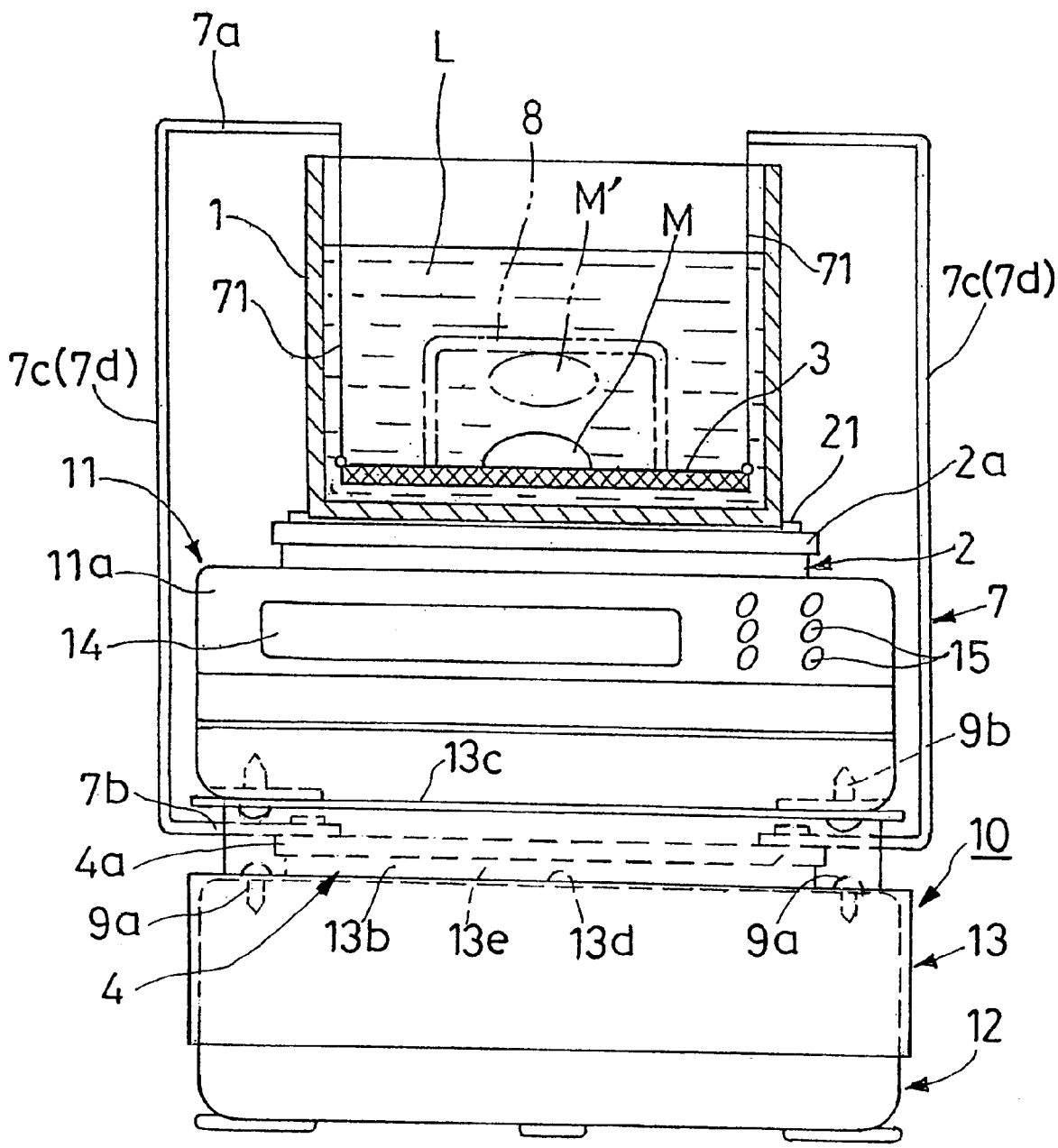
FIG. 1 is a front elevation of the overall construction of one embodiment of a specific gravity measuring device according to the present invention, in which a liquid bath portion is illustrated in sections.
Figure 2:
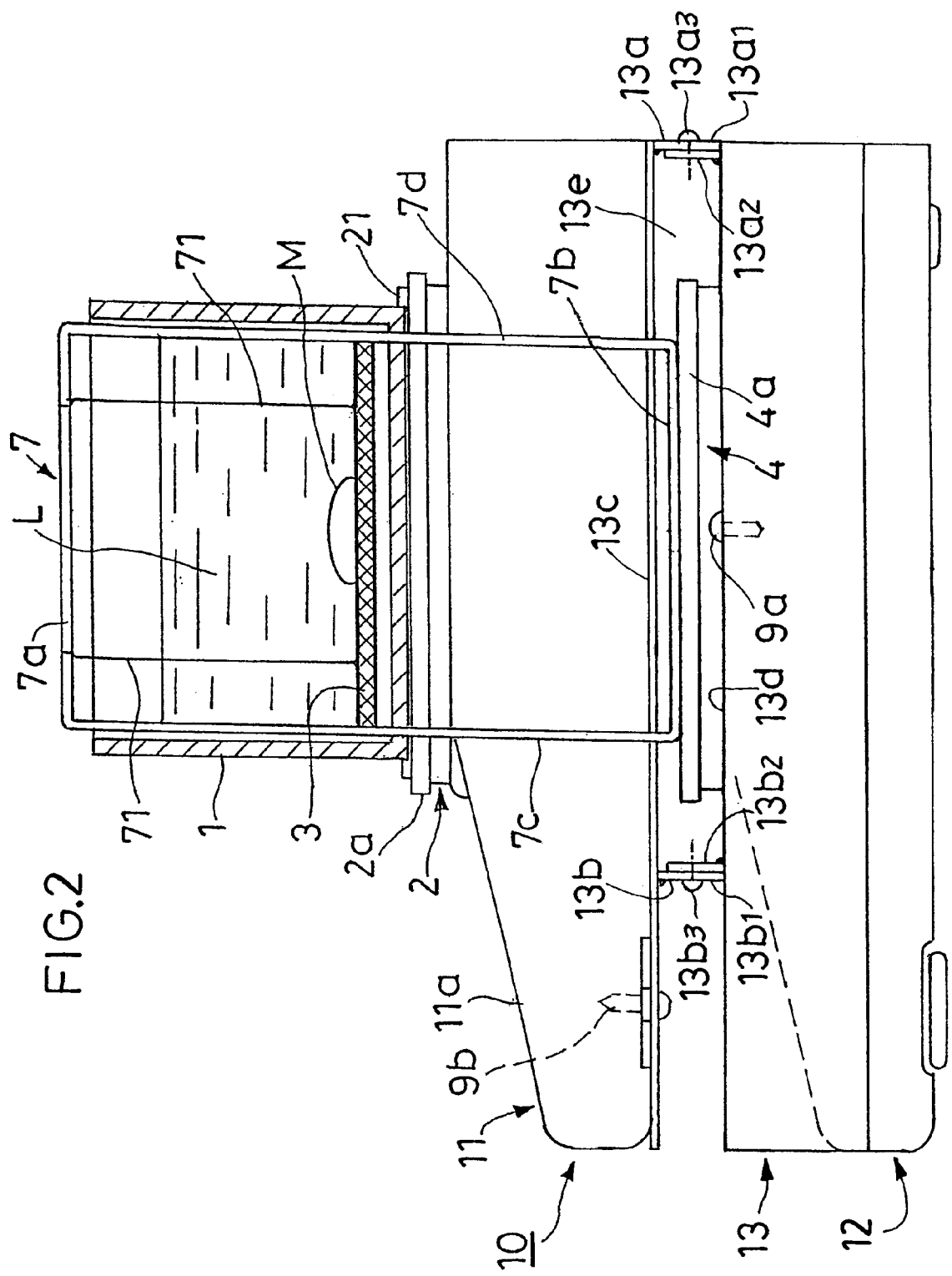
FIG. 2 is a side elevation of the entire specific gravity measuring device according to the present invention, in which a liquid bath portion is illustrated in section.
Figure 3:
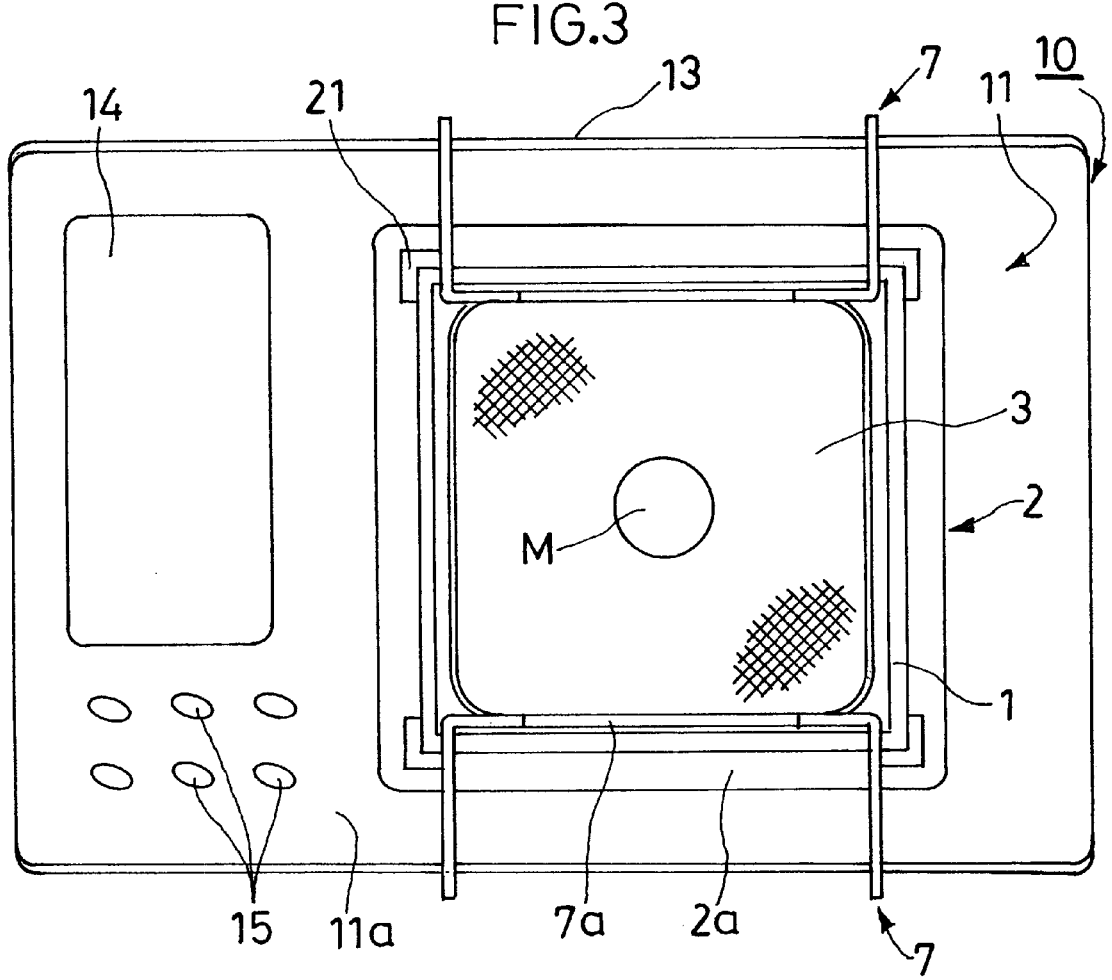
FIG. 3 is a plan view of the entire specific gravity measuring device according to the present invention.

FIG. 1 is a front elevation of the overall construction of one embodiment of a specific gravity measuring device according to the present invention, in which a liquid bath portion is illustrated in section, FIG. 2 is a side elevation of the entire specific gravity measuring device according to the present invention, in which a liquid bath portion is illustrated in section, and FIG. 3 is a plan view of the entire specific gravity measuring device according to the present invention.

As shown in FIGS. 1 and 2, a specific gravity measuring device is constructed by forming a measuring body 10 by integrally coupling an upper first weighting equipment 11 forming a first measuring portion 2 and a lower second weighting equipment 12 forming a second measuring portion 4 in two stages. A sectionally quadrangular liquid bath 1 filled with water L is received and supported on a receptacle seat 2a of the first measuring portion 2. In the liquid bath 1, a quadrangular dish shaped measuring object receptacle member 3 in mesh structure is arranged in sinking condition.

Particularly, a box shaped connection frame 13 fitted over the second weighting equipment 12 is fixed on an upper surface of the second weighting equipment with an upper surface plate portion 13d by means of fastening screws 9a. Then, on front and back sides of the upper surface plate portion 13d of the connection frame 13, space holding plates 13a and 13b extending vertically are formed integrally. On the space holding plates 13a and 13b, an upper plate 13c is integrally fixed. The upper plate 13c is rigidly secured on a bottom portion of the first weighting equipment 11 by means of fastening screws 9b. Accordingly, the second weighting equipment 12 and the first weighting equipment 11 are integrally held in spaced apart relationship defining a gap portion 13e therebetween by the space holding plates 13a and 13b located at front and rear sides. It should be noted that the space holding plates 13a and 13b are formed by vertically extending projecting plates $13a_1$, $13a_2$, $13b_1$, and $13b_2$ in mutually opposing relationship and mutually fastening mating projecting plates $13a_1$, $13a_2$ and $13b_1$, $13b_2$ by means of fastening screws $13a_3$ and $13b_3$. However, construction of the space holding plates 13a and 13b is not limited to that specified in the shown embodiment but may be embodied in various manner. The first weighting equipment 11 is built in an arithmetic unit 5 constituted of a microcomputer, and a display unit 6 (see FIG. 4). On a front tilted upper surface 11a, a display panel 14 and operation buttons 15 are provided as shown in FIG. 3.

The receptacle seat 2a of the first measuring portion 2 has positioning projections 21 at four corners on the upper surface. Upon mounting the liquid bath 1 on the receptacle seat 2a, a quadrangular bottom surface of the liquid bath 1 is engaged to set the liquid bath 1 at a predetermined position. On the other hand, naturally, a receptacle seat 4a of the second measuring portion 4 is formed separately from the connection frame 13 and is located downwardly spaced apart from the upper plate 13c of the connection frame 13. Namely, while not illustrated, the upper surface plate portion 13d of the connection frame is formed with an opening at a portion where the receptacle seat 4a is positioned so as not to contact with the receptacle seat 4a. By a pair of left and right hanging members 7 extending upwardly from the receptacle seat 4a, the measuring object receptacle member 3 is hanged relative to the liquid bath 1 in non-contacting condition.

The hanging members 7 are formed into a substantially quadrangular frame shape with horizontally extending channel-shaped upper and lower portions 7a and 7b and vertically extending front and rear support portions 7c and 7d formed by bending one metal thick wire. Both support portions 7c and 7d are arranged in spaced apart positions outside of the first weighting equipment 11. The horizontally extending channel-shaped lower portions 7b extend inwardly from the lower end of the support portions 7c and 7d and are rigidly secured on the receptacle seat 4a. On the other hand, on the horizontally extending channel-shaped upper portions 7a extending inwardly from the upper end of the support portions 7c and 7d beyond the upper edge of the liquid bath 1, the measuring object receptacle member 3 is hanged by two cables 71. Thus, the horizontal channel-shaped lower portions 7b are connected to the lower end of both support portions 7c and 7d through the gap portion 13e defined by the front and rear space holding plates 13a and 13b to maintain the hanging members 7 in non-contact condition relative to the connection frame 13.

As set forth above, as the specific gravity measuring device, weighting mechanism and arithmetic and display portion are housed within the main body of the weighting equipment, and the liquid bath receiving the measuring objective receptacle member is arranged above the main body of the weighting equipment to functionalbly aggregate the overall device to provide neat and good appearance. Also, since the measuring object receptacle member is hanging type, placement within the liquid bath, removal from the liquid bath for washing or for other purpose can be done easily.

Figure 4:
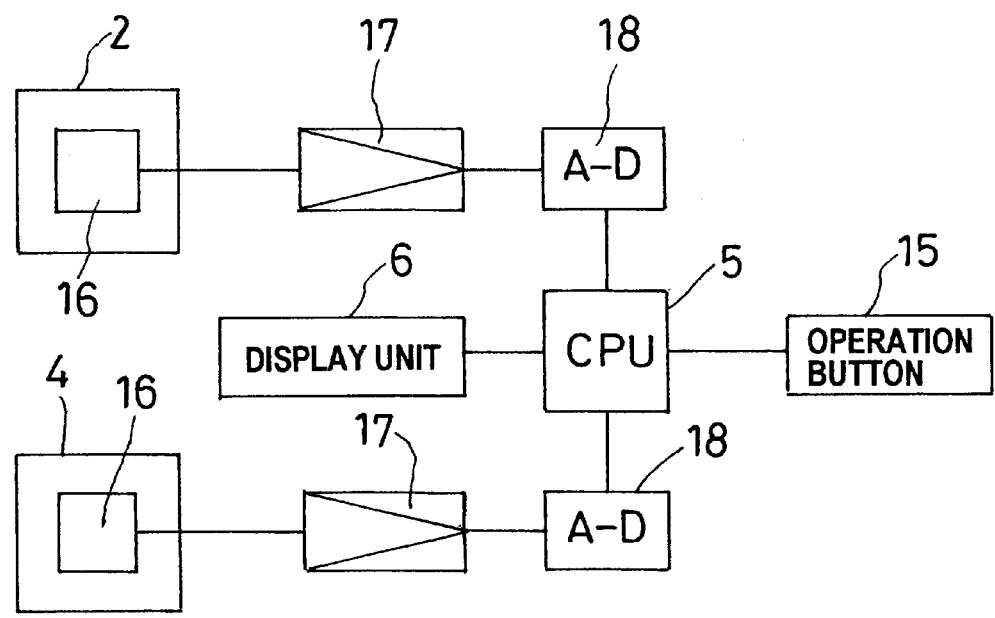
FIG. 4 is a block diagram of a measuring and displaying mechanism portion of the specific gravity measuring device of the present invention.

Referring to FIG. 4, the first measuring portion 2 and the second measuring portion 4 convert weight load applied to the receptacle seats 2a and 4a into electrical signals by weight sensitive sensor 16. The electrical signals are amplified by amplifiers 17 to output as analog signals having values corresponding to the applied weight loads. The analog signals are converted into digital signals by A/D converters 18 to input to an arithmetic unit 5. Then, the arithmetic unit 5 calculates specific gravity on the basis of the input signals from the first measuring portion 1 and the second measuring portion 2 to display the derived value on a display panel 14 in the display unit 6. It should be noted that the operation buttons 15 includes a power switch turning ON and OFF a power source, a measurement start switch, and in addition thereto, various function buttons, such as a water temperature dependent correction button, an atmospheric density dependent correction button, a liquid specific gravity input button and/or a liquid kind selection button which will be used when a liquid other than water is used, and so forth.

For measuring specific gravity of the measuring object M by the specific gravity measuring device constructed as set forth above, an appropriate amount of water L is preliminarily filled in the liquid bath 1. Before placing the measuring object M within the liquid bath 1, measurement start is commanded by the operation button 15, weights of the first measuring portion 2 and the second measuring portion 4 are measured in a condition where the measuring object M is not loaded, to set zero points for reference. Thus, the device becomes a condition ready for measurement. Then, the measuring object M is placed within the liquid bath 1 to mount on the measuring object receptacle member 3 in sinking condition. As soon as the water surface of the water L becomes stable, specific gravity value is automatically calculated and displayed. It is, of course, possible to set so that measurement of specific gravity of the measuring object M is initiated by manually commanding measurement start by the operation button 15. In the second measuring portion 4, increase of weight after loading the measuring object M is measured as weight of the measuring object M in water. On the other hand, since the weight in water is not loaded on the liquid bath 1, increase of the weight measured by the first measuring portion 2 represents increase of water L corresponding to volume of the measuring object M, namely buoyancy.

Here, since specific gravity of water L is 1, [weight in air=weight in water+buoyancy] is established. From the following expression, $$\text{Specific Gravity}=\text{Weight in Air}/\text{Buoyancy}=(\text{Weight in Water}+\text{Buoyancy})/\text{Buoyancy}$$

specific gravity can be derived from the measured value of the weight in water and buoyancy without measuring the weight in air. Accordingly, specific gravity can derived by the arithmetic unit 5 by the foregoing equation. The derived value is displayed on the display panel 14 via the display unit 6.

In the foregoing process of measurement of specific gravity, it becomes unnecessary to measure the weight of the measuring object M in air, and specific gravity can be obtained by simultaneously measuring the buoyancy and weight in liquid by the first measuring portion 2 and the second measuring portion 4 only by mounting the measuring object M on the measuring object receptacle member 3 within the liquid bath 1 in sinking condition. Therefore, the measurement of specific gravity according to the present invention is less troublesome and takes shorter period comparison with the conventional specific gravity measuring process requiring two stages of measurement operation, Particularly, the measurement of specific gravity according to the present invention is quite efficient when measurement of specific gravities of different measuring objects M are measured sequentially. It should be noted that the measuring object M is removed from the liquid bath 1 in wet condition after measurement and thus water L is reduced in the amount wetting the measuring object M, error in measurement due to variation of water amount can be canceled by resetting the zero point in advance of next measurement.

It should be noted that while the shown embodiment has been discussed in terms of specific gravity measurement with assumption that specific gravity of water L is 1, water has specific gravity 1 at 4° C. in strict sense. When strict specific gravity measurement is necessary, correction of the measured value depending upon water temperature can be performed. As means therefor, a water temperature dependent correction program is loaded in the arithmetic unit 5 to measure water temperature to input to the arithmetic unit 5 upon specific gravity measurement, for example. In the alternative, a temperature sensor for detecting water temperature in the liquid bath 1 is provided, and the measured water temperature by the temperature sensor is automatically input as electric signal.

On the other hand, in the shown embodiment, water is used as liquid to be filled in the liquid bath 1. However, when the measuring object M is a material which requires avoidance of contact with water, an appropriate liquid having known specific gravity may be used depending upon the material. Therefore, when the liquid other than water is used, the specific gravity of the measuring object M is derived by multiplying the value derived on the basis of the buoyancy measured by the first measuring portion and the weight in liquid measured by the second measuring portion in similar manner as that set forth above, by specific gravity of the liquid used. Then, similar to the case of correction depending upon water temperature, a program for deriving specific gravity of the light is preliminarily loaded in the arithmetic device 5 to input specific gravity of the used liquid, or to select kind of the liquid to be used by the operation button 15 when kinds of the liquids to be used are preliminarily determined.

Also, in the specific gravity measuring device according to the present invention, when specific gravity of the measuring object M' smaller than that of the liquid in the liquid bath 1, the measuring object M' cannot be measured the weight in liquid and buoyancy as floating up in the liquid. For example, as shown by phantom line in FIG. 1, a floating preventing member 8 formed of a heavy material, such as metal, is mounted on the measuring object receptacle member 3, and the measuring object M' is placed inside of the floating preventing member 8 to maintain the measuring object on the measuring object receptacle member 3 in sinking condition. At this time, setting of zero point is performed in the condition where the floating preventing member 8 is placed on the measuring object receptacle member 3. The weight of the measuring object M' in liquid is measured as negative value.

By using the floating preventing member 8 as set forth above, not only substances formed of per se light weight material, such as synthetic resin, rubber, foamed body thereof but also hollow substance, such as ball, capsule or the like, can be measured specific gravity. However, since the floating preventing member 8, it is merely required to hold the measuring object M' on the measuring object receptacle member 3 in sinking condition, member which can be engaged with the measuring object receptacle member 3 or member which is formed integrally with the measuring object receptacle member, for retaining the measuring substance on the measuring object receptacle member, can be employed in place of the member formed of heavy material. In case of former mounting type floating preventing member, greater weight is required for greater buoyancy of the measuring object M', whereas, in case of the engaging type or integral type floating preventing member, it can be used irrespective of own weight. On the other hand, shape of the floating preventing member 8 is not particularly specified depending upon the shape of the measuring object M' as long as the loading and unloading of the measuring object M' can be easily performed and floating of the measuring object M' away from the measuring object receptacle member can be certainly prevented.

As the measuring object receptacle member 3, in addition to the dish shape as in the shown embodiment, various shapes, such as, a plate shape, flat plate shape with upwardly projecting edge extending circumferentially for preventing drop down, a bowed plate shape, a reversed cone shape, a basket shape, a vessel shape and so forth, may be used. Also, concerning outer shape, various shape, such as triangular shape, square, rectangular, polygonal shape more than or equal to pentagonal shape, circular shape, elliptic shape and so forth, can be set arbitrarily. Also, the structure of the measuring object receptacle member 3 may be a structure using porous plate, such as punching metal, a structure provided with apertures or slits for liquid flow in necessary portions and so forth, other than mesh structure. Furthermore, while a structure to hang the measuring object receptacle member 3 by the hanging member 7 through the cables 71 in the shown embodiment, a structure to rigidly support the measuring object receptacle member 3 on the second measuring portion 4 may also be employed. However, the hanging type measuring object receptacle member 3 is preferred for easiness of installation within the liquid bath 1 in non-contact condition and removal from the liquid bath 1 for washing or other purpose.

It should be noted that each of the left and right hanging members 7 has structure in the shown embodiment, in which the horizontally extending channel-shaped lower portions 7a are integrated with upper end of each of front and rear support portions 7c and 7d. However, various shapes of hanging members may be employed. As particular example, a structure, in which an upper end of each of left and right single support portion is bifurcated, the bifurcated portions are projected inwardly over the liquid bath 1 and cables 71 for hanging the measuring object receptacle member 3 are depended from the tip ends of the bifurcated portions, a structure, in which respectively two mutually independent support portions are placed on left and right sides, the upper portions of respective support portions are bent inwardly over the liquid bath 1, and the cables 71 are depended from the tip ends of the support portions, or a structure, in which upper portions of respective one left and right support portions are bent inwardly over the liquid bath 1, two cables 71 are depended from the tip ends of the support portions and the measuring object receptacle member 3 are depended with spacing apart the lower end side of the cables 71, or a structure, in which upper ends of two support portions on left and right sides are connected by lateral rods, one or two support arms or channel-shaped support frames are inwardly projected over the liquid bath 1 from the lateral rod, and the cables are depended from the support arms or support frame, may be employed. Also, the outer shape of the measuring object receptacle member 3 is circular shape, triangular shape, hexagonal shape or so forth, three cables may be employed for hanging the measuring object receptacle member 3 for three points support structure. Then, number of support portions and shape thereof may be selected arbitrarily.

While the weighting main body 10 is constructed by integrating the first and second weighting equipments 11 and 12 via the connection frame 13 in the shown embodiment, it is also possible to assembly the first measuring portion 2 and the second measuring portion 4 within one casing. Also, the specific gravity measuring device according to the present invention may be modified in various design in addition to the embodiment, in terms of the shape, structure and so forth of respective components and detailed construction, as well as the shape of the liquid bath 1.

As the measuring object M, in addition to various known materials, such as metal, synthetic resin, ceramics, rubber, fiber, powder state measuring object, granular state measuring object may also be measured specific gravities in a form received within an appropriate container which performing flow of the liquid K therein (zero point is set in a condition where the empty container is sunk in the liquid). Furthermore, concerning the liquid, specific gravity may also be measured in a form contained in an appropriate container when the liquid as measuring object is not admixed with the liquid L in the liquid bath 1 and has specific gravity greater than the liquid L. On the other hand, when water is used as the liquid L in the liquid bath 1, bubble may be generated by dissolved gas component associating with variation of temperature. If such bubble adhere on the measuring object receptacle member 3, error in measurement depending on buoyancy can be caused. Therefore, in order to prevent the bubble from adhering, surface active agent may be added.

On the other hand, it is possible to mount a memory device in the microcomputer forming the arithmetic unit to store the resultant measured specific gravity. Concerning display in the display unit 6, it is possible to display not only specific gravity, but also result of decision of pass or fall or telling the real from false as product by comparing the measured specific gravity with data stored in the memory device. Furthermore, concerning functions of the arithmetic unit or the display unit, it is also possible to use external controller, such as personal computer connected to the main body of the weighting equipment instead of building in the main body of the weighting equipment. In addition, it is also possible to automatically perform loading and unloading of the measuring object M in and out the liquid bath 1 by means of robot or the like pr to build in the specific gravity measuring device according to the present invention together with the robot in inspection line or manufacturing line having automatic transporting apparatus of the measuring object.

What is claimed is:

1. A specific gravity measuring device comprising:
    a liquid bath filled with a liquid;
    a first measuring portion receiving and supporting said liquid bath;
    a measuring object receptacle member arranged in said liquid bath in a condition dipped in said liquid;
    a second measuring portion supporting said measuring object receptacle member in non-contact condition relative to said liquid bath;
    an arithmetic unit deriving a specific gravity value on the basis of measured values of said first and second measuring portions; and
    a display unit for displaying the specific gravity value derived by said arithmetic unit;
    said measuring object being mounted on said measuring object receptacle member sinking in the liquid within said liquid bath in a condition sinking in the liquid;
    said first measuring portion measuring increase of weight associating with dipping of said measuring object in the liquid by said first measuring portion, as buoyancy;
    said second measuring portion acting simultaneously with said first measuring portion and measuring a weight of said measuring object in the liquid by said second measuring portion;
    said arithmetic unit deriving said specific gravity value from a measured value of the buoyancy and the weight in liquid for displaying on said display unit.

2. A specific gravity measuring device as set forth in claim 1, wherein said arithmetic means is provided with arithmetic correction means.

3. A specific gravity measuring device as set forth in claim 1, wherein said measuring object receptacle member is porous member, such as net form member.

4. A specific gravity measuring device as set forth in claim 1, wherein said first measuring portion, said second measuring portion, said arithmetic unit and said display unit are integrally assembled in a main body of weighting equipment, and said measuring object receptacle member is hanged by hanging member vertically extending from said second measuring portion.

5. A specific gravity measuring device as set forth in claim 4, wherein said main body of said weighting equipment is constructed with a first weighting equipment forming said first measuring portion and a second weighting equipment forming said second measuring portion, said first and second weighting equipments are integrally connected by a connection frame with defining a gap portion there between.

6. A specific gravity measuring device as set forth in claim 4, wherein said hanging member is a wire member including a lower horizontal member fixed to a receptacle seat of said second measuring portion, a support member extending upwardly from said lower horizontal member and an upper horizontal member extending from upper end portions of said support member beyond an upper edge of said liquid bath and extending horizontally in opposition to an upper surface of said liquid bath.

7. A specific gravity measuring device as set forth in claim 6, wherein said measuring object receptacle member is hanged by a cable connected to said upper horizontal member at the upper portion and depending into said liquid bath.

8. A specific gravity measuring device as set forth in claim 1, which further comprises a floating preventing member for holding a measuring object lighter than the liquid in said liquid bath on said measuring object receptacle member in sinking condition.

9. A specific gravity measuring device comprising:
    a liquid bath containing a liquid having known specific gravity;
    measuring object mounting means disposed within said liquid bath for mounting a measuring object in a condition sinking in said liquid;

first measuring means for directly receiving weight of said liquid bath and deriving a buoyancy indicative value representative of buoyancy of said measuring object on the basis of a weight increase when said measuring object is placed on said measuring object mounting means and known specific gravity of said liquid;

second measuring means for supporting said measuring object mounting means, directly receiving weight of said measuring object mounting means and said measuring object as placed on the former and deriving a weight in liquid indicative value representative of weight of said measuring object in liquid;

arithmetic means for receiving said buoyancy indicative value and said weight in liquid indicative value for deriving a specific gravity indicative value representative of specific gravity of said measuring object; and display means for displaying said specific gravity indicative value.

10. A specific gravity measuring device as set forth in claim 9, which further comprises initial setting means for setting initial value of said buoyancy indicative value and said weight in liquid indicative value in a condition where said measuring object is not loaded on said measuring object mounting means.

11. A specific gravity measuring device as set forth in claim 9, wherein said second measuring means supports said measuring object mounting means in floating condition relative to said liquid bath.

12. A specific gravity measuring device as set forth in claim 9, which further comprises retainer means for retaining said measuring object on said measuring object mounting means.

13. A specific gravity measuring device comprising:

a liquid bath containing a liquid having known specific gravity;

measuring object mounting means disposed within said liquid bath for mounting a measuring object in a condition sinking in said liquid;

first measuring means for directly receiving weight of said liquid bath and deriving a liquid bath weight indicative value representative of a liquid bath weight;

second measuring means for supporting said measuring object mounting means, directly receiving weight of said measuring object mounting means and said measuring object as placed on the measuring object mounting means and deriving a weight in liquid indicative value representative of weight of said measuring object in liquid;

arithmetic means for receiving said liquid bath indicative value and said weight in liquid indicative value for deriving a buoyancy indicative value on the basis of variation of said liquid bath weight indicative values before and after mounting said measuring object on said measuring object mounting means and said known specific gravity of said liquid, and further deriving a specific gravity indicative value representative of specific gravity of said measuring object on the basis of said buoyancy indicative value and said weight in liquid indicative value; and display means for displaying said specific gravity indicative value.

* * * * *